United States Patent
Kloos

(10) Patent No.: US 9,309,539 B2
(45) Date of Patent: Apr. 12, 2016

(54) SYSTEM FOR RECYCLING WATER TO FACILITATE THE PRODUCTION OF ETHANOL

(75) Inventor: Rachel L. Kloos, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 1386 days.

(21) Appl. No.: 12/757,630

(22) Filed: Apr. 9, 2010

(65) Prior Publication Data

US 2010/0261243 A1 Oct. 14, 2010

Related U.S. Application Data

(60) Provisional application No. 61/168,334, filed on Apr. 10, 2009.

(51) Int. Cl.
*C12P 7/06* (2006.01)
*C12M 1/00* (2006.01)

(52) U.S. Cl.
CPC *C12P 7/06* (2013.01); *C12M 21/12* (2013.01); *Y02E 50/17* (2013.01)

(58) Field of Classification Search
CPC ................ C12P 7/06; C12P 7/08; C12P 7/10; C12M 21/12
USPC .............................................. 435/161, 289.1
See application file for complete search history.

(56) References Cited

U.S. PATENT DOCUMENTS

| 4,503,079 A | 3/1985 | King et al. |
| 4,617,270 A * | 10/1986 | Anderson et al. ............. 435/161 |
| 7,810,425 B1 * | 10/2010 | Kessler ........................... 99/276 |
| 2004/0234649 A1 * | 11/2004 | Lewis et al. ..................... 426/31 |
| 2008/0047897 A1 | 2/2008 | Jeong et al. |

OTHER PUBLICATIONS

International Search Report mailed Aug. 4, 2010 for PCT Application Serial No. PCT/US10/30600, 13 pages.

* cited by examiner

*Primary Examiner* — William H Beisner
(74) *Attorney, Agent, or Firm* — Amin, Turocy & Watson, LLP

(57) ABSTRACT

A system for the production of ethanol is disclosed. The system comprises a system for recycling water in an ethanol production process. The system may comprise: a water supply that supplies water to the ethanol production process, a cooling tower system that supplies water to the ethanol production process, and a treatment system that supplies water to the ethanol production process. The treatment system may be a reverse osmosis system that supplies a retentate stream to the ethanol production process.

11 Claims, 11 Drawing Sheets

Source Water

| Component | Typical Concentration (ppm) | Example Flow 393 gal/min Concentration (ppm) |
|---|---|---|
| Ca | 90-200 | 108 |
| Mg | 20-70 | 37 |
| $SO_4$ | 10-100 | 24 |
| $SiO_2$ | 20-70 | 32 |
| Cl | 40-80 | 45 |
| Total Dissolved Solids | 600-1500 | 704 |

FIG. 5

Reverse Osmosis Permeate

| Component | Typical Concentration (ppm) | Example Flow 280 gal/min Concentration (ppm) |
|---|---|---|
| Ca | < 10 | 2.5 |
| Mg | < 5 | 0.9 |
| $SO_4$ | < 2 | 0.2 |
| $SiO_2$ | < 4 | 1.0 |
| Cl | < 10 | 1.9 |
| Total Dissolved Solids | < 20 | 18.5 |

FIG. 6

Reverse Osmosis Retentate

| Component | Typical Concentration (ppm) | Example Flow 93 gal/min Concentration (ppm) |
|---|---|---|
| Ca | 225-500 | 425 |
| Mg | 50-175 | 144 |
| $SO_4$ | 100-500 | 293 |
| $SiO_2$ | 60-125 | 124 |
| Cl | 100-250 | 174 |
| Total Dissolved Solids | 1500-3000 | 2760 |

FIG. 7

Cooling Tower Discharge

| Component | Typical Concentration (ppm) | Example Flow 22 gal/min Concentration (ppm) |
|---|---|---|
| Ca | 100-200 | 130 |
| Mg | 30-60 | 48 |
| $SO_4$ | 10-50 | 24 |
| $SiO_2$ | 10-60 | 42 |
| Cl | 40-80 | 65 |
| Total Dissolved Solids | 800-1500 | 876 |

FIG. 8

Water to Ethanol Production Process

| Component | Operating Range Concentration (ppm) | Preferred Concentration (ppm) | Most Preferred Concentration (ppm) | Example Flow 115 gal/min Concentration (ppm) |
|---|---|---|---|---|
| Ca | 100-600 | 250-450 | 325-380 | 368 |
| Mg | 30-600 | 50-200 | 100-150 | 125 |
| $SO_4$ | 10-500 | 200-300 | 225-275 | 242 |
| $SiO_2$ | 0-125 | 60-110 | 80-100 | 108 |
| Cl | 0-250 | 100-175 | 125-160 | 153 |
| Total Dissolved Solids | 1000-4000 | 1500-2500 | 1800-2200 | 2400 |

FIG. 9

Sources of Water to Ethanol Production Process

| Source | Operating Range (percent) | Preferred Range (percent) | Most Preferred Range (percent) |
|---|---|---|---|
| Water Supply | up to 100 | 60 – 90 | 70 – 80 |
| Cooling Tower Discharge | < 10 | 1 – 7 | 2 – 4 |
| Reverse Osmosis Retentate | < 30 | 10 – 25 | 15 – 20 |
| Steam | 0 – 5 | 1 – 3 | 1.8 – 2.2 |

FIG. 10

SYSTEM FOR RECYCLING WATER TO FACILITATE THE PRODUCTION OF ETHANOL

CROSS-REFERENCE TO RELATED APPLICATIONS

The present application claims the priority of and expressly incorporates by reference the following application: U.S. Provisional Patent Application Ser. No. 61/168,334, entitled "WATER REDUCTION DESIGN FOR ETHANOL PRODUCTION," which was filed on Apr. 10, 2009.

TECHNICAL FIELD

The present application relates to a system that reduces water usage in the production of ethanol by recycling water. The present application also relates to a method of recycling water in an ethanol production process in a biorefinery. The present application further relates to a biorefinery employing a system that recycles water in the ethanol production process.

BACKGROUND

Ethanol can be produced from grain-based feedstocks (e.g., corn, sorghum/milo, barley, wheat, soybeans, etc.), from sugar (e.g., sugar cane, sugar beets, etc.), or from biomass (e.g., lignocellulosic feedstocks, such as switchgrass, corn cobs and stover, wood, or other plant material).

In a conventional ethanol plant, corn is used as a feedstock and ethanol is produced from starch contained within the corn. Corn kernels are cleaned and milled to prepare starch-containing material for processing. Corn kernels can also be fractionated to separate the starch-containing material (e.g., endosperm) from other matter (such as fiber and germ). The starch-containing material is slurried with water and liquefied to facilitate saccharification, where the starch is converted into sugar (e.g., glucose), and fermentation, where the sugar is converted by an ethanologen (e.g., yeast) into ethanol. The fermentation product is beer, which comprises a liquid component, including ethanol, water, and soluble components, and a solids component, including unfermented particulate matter (among other things). The fermentation product is sent to a distillation system where the fermentation product is distilled and dehydrated into ethanol. The residual matter (e.g., whole stillage) comprises water, soluble components, oil, and unfermented solids (e.g., the solids component of the beer with substantially all ethanol removed, which can be dried into dried distillers grains (DDG) and sold, for example, as an animal feed product). Other co-products (e.g., syrup and oil contained in the syrup), can also be recovered from the whole stillage. Water removed from the fermentation product in distillation can be treated for re-use at the plant.

Water utilized in the production of ethanol can be obtained from many different sources (e.g., ground well water, surface water, or municipal water), resulting in different water qualities. Water used in the generation of steam may be filtered (e.g., by reverse osmosis) to reduce the level of dissolved solids. Water that contains the dissolved solids (e.g., reverse osmosis reject) is removed and dispensed.

It would be advantageous to provide for a system that reduces water usage in the production of ethanol. It would also be advantageous to provide for a system that captures and uses waste water streams as a way to reduce overall water usage in the production of ethanol. It would further be advantageous to provide for a method for balancing the total dissolved solids, suspended solids, and other minerals and ions to reduce water usage in the production of ethanol.

SUMMARY

The present invention relates to a method of recycling water in an ethanol production process in a biorefinery. The biorefinery comprises a water supply, a cooling tower system, a treatment system and a boiler system. The method of recycling water in the ethanol production process comprises the steps of supplying water from the water supply to the ethanol production process, supplying water from the cooling tower system to the ethanol production process, and supplying water from the treatment system to the ethanol production process.

The present invention also relates to a system for recycling water in an ethanol production process in an ethanol production facility. The water recycling system comprises a water supply that supplies water from the water supply to the ethanol production process. The water recycling system also comprises a cooling tower system that supplies water from the cooling tower system to the ethanol production process. The water recycling system further comprises a treatment system that supplies water from the treatment system to the ethanol production process.

The present invention further relates to a biorefinery. The biorefinery comprises an ethanol production system that performs an ethanol production process. The biorefinery further comprises a water recycling system that supplies water to the ethanol production process. The water recycling system comprises a water supply, a cooling tower system, and a treatment system. The water supply supplies less than 100 percent of the water to the ethanol production process, the cooling tower system supplies less than 10 percent of the water to the ethanol production process, and the treatment system supplies less than 30 percent of the water to the ethanol production process.

BRIEF DESCRIPTION OF THE DRAWINGS

FIG. 5 is a table of exemplary operating ranges for dissolved solids concentration in source water from a water supply.

FIG. 6 is a table of exemplary operating ranges for dissolved solids concentration in a permeate stream from a reverse osmosis system.

FIG. 7 is a table of exemplary operating ranges for dissolved solids concentration in a retentate stream from a reverse osmosis system.

FIG. 8 is a table of exemplary operating ranges for dissolved solids concentration in discharge from a cooling tower system.

FIG. 9 is a table of exemplary operating ranges for dissolved solids concentration in water supplied to an ethanol production process.

FIG. 10 is a table of exemplary operating ranges for sources of water supplied to an ethanol production process.

DETAILED DESCRIPTION

Figure 1:
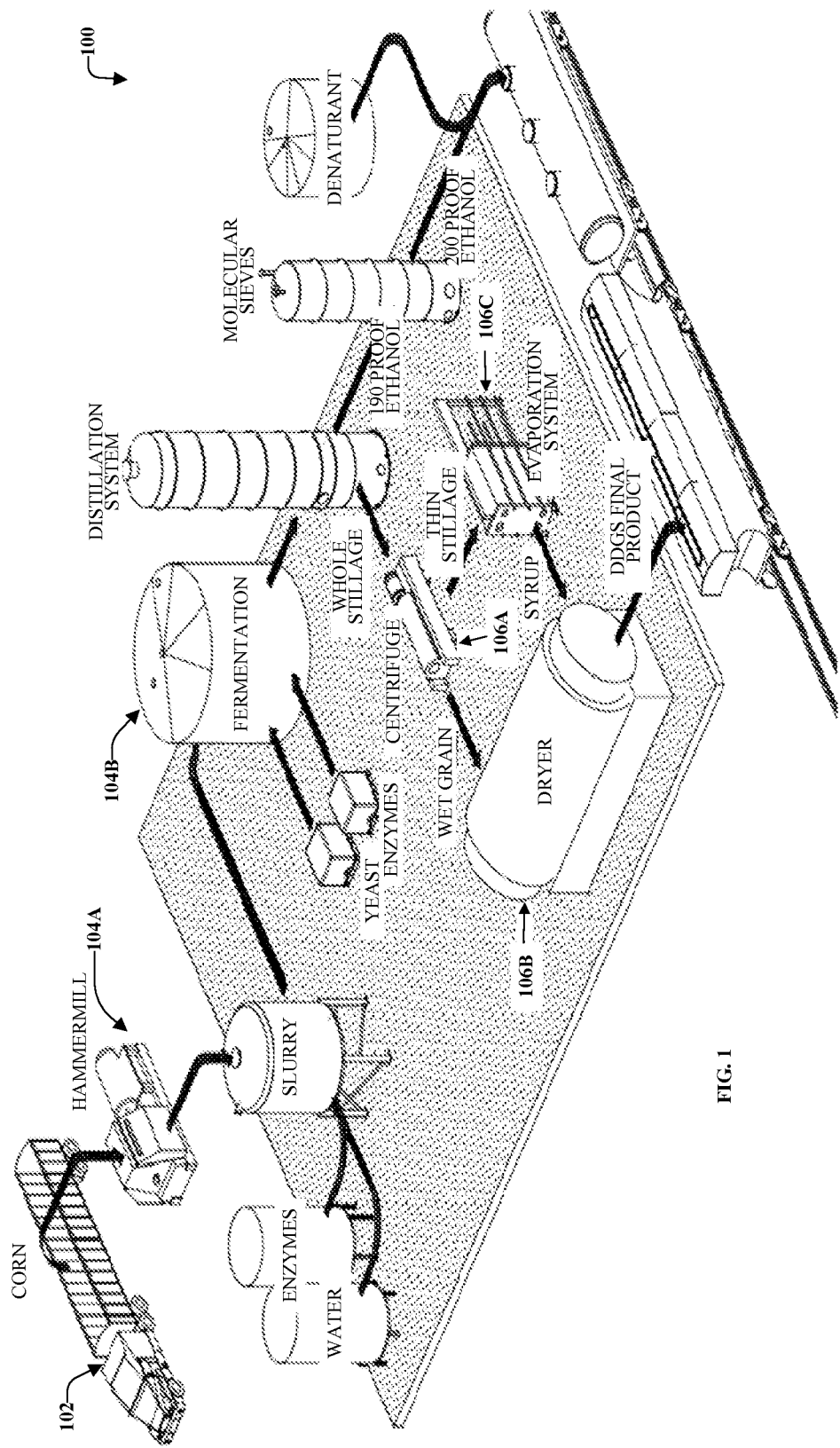
FIG. 1 is a perspective view of a biorefinery comprising a corn-based ethanol production facility.

Referring to FIG. 1, a biorefinery 100 comprising an ethanol production facility configured to produce ethanol from corn is shown. The biorefinery 100A comprises an area 102 where corn is delivered and prepared to be supplied to the ethanol production facility. The ethanol production facility comprises apparatus 104A for preparation and treatment (e.g. milling) of the corn into corn flour suitable for fermentation into fermentation product in a fermentation system 104B. The ethanol production facility comprises a distillation system 104C in which the fermentation product is distilled and dehydrated into ethanol. As shown in FIG. 1A, the biorefinery 100 may also comprise a by-product treatment system (shown as comprising a centrifuge 106A, a dryer 106B and an evaporator 106C).

Figure 2A:
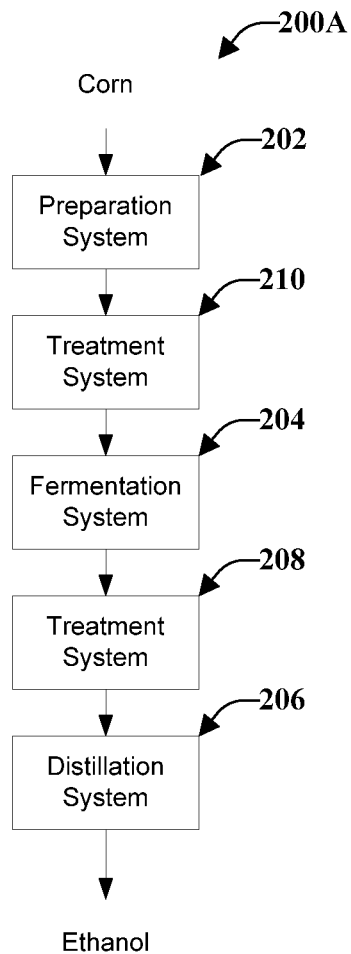
FIGS. 2A, 2B and 2C are schematic block diagrams of an ethanol production process.
Figure 2B:
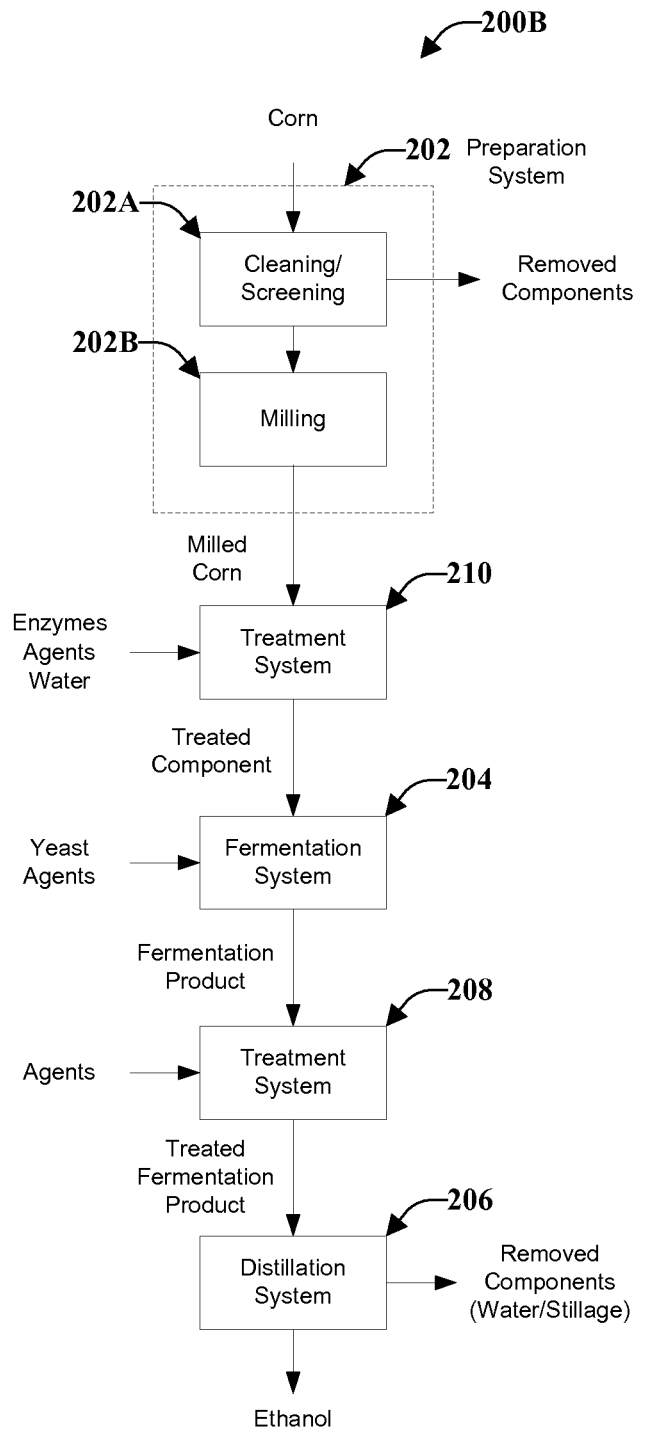
Figure 2C:
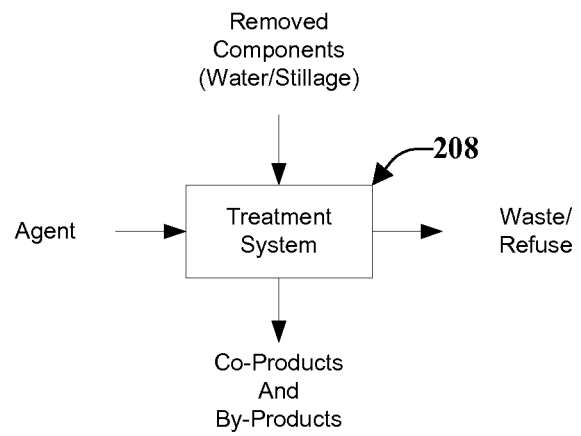

Referring to FIGS. 2A and 2B, in an ethanol production process 200A and 200B, corn can be prepared for further treatment in a preparation system 202. As seen in FIG. 2B, the preparation system 202 may comprise a cleaning 202A or screening 202B step to remove foreign material, such as rocks, dirt, sand, pieces of corn cobs and stalk, and other unfermentable material. After cleaning/screening, the particle size of corn can be reduced by milling to facilitate further processing. The corn kernels may also be fractionated into starch-containing endosperm and fiber and germ. The milled corn or endosperm is slurried with water, enzymes and agents to facilitate the conversion of starch into sugar (e.g. glucose). The sugar is converted into ethanol by an ethanologen (e.g. yeast) in a fermentation system 204. The product of fermentation (i.e. fermentation product) is beer, which comprises a liquid component, including ethanol and water and soluble components, and a solids component, including unfermented particulate matter (among other things). The fermentation product is sent to a distillation system 206. In the distillation system, the fermentation product is distilled and dehydrated into ethanol. As shown in FIG. 2C, the removed components (e.g., whole stillage), which comprise water, soluble components, oil and unfermented solids (e.g., the solids component of the beer with substantially all ethanol removed), can be dried into dried distillers grains (DDG) and sold as an animal feed product. Other co-products, for example, syrup (and oil contained in the syrup), can also be recovered from the stillage. Water removed from the fermentation product in distillation can be treated for re-use at the plant.

Figure 3A:
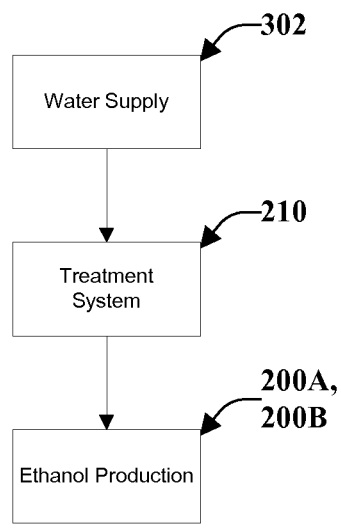
FIGS. 3A and 3B are schematic block diagrams of water filtration in an ethanol production facility.
Figure 3B:
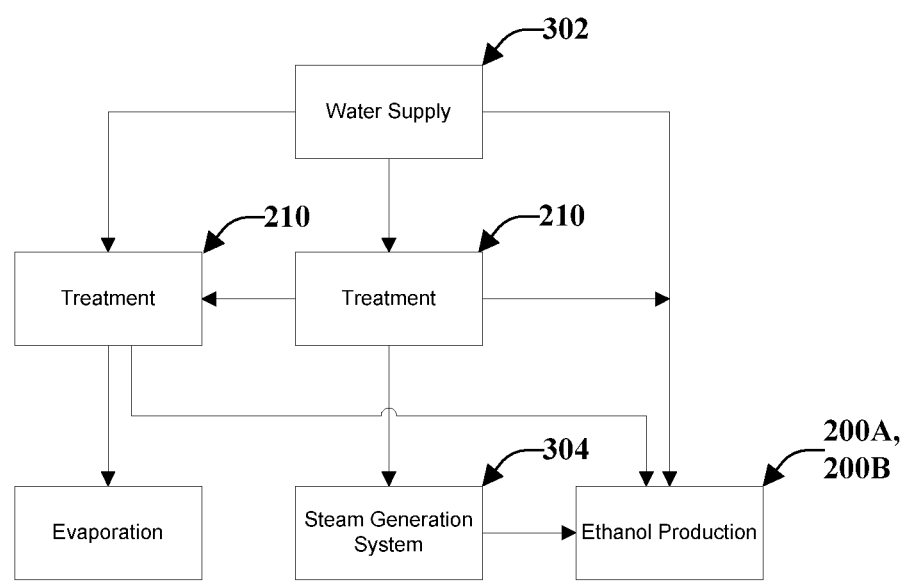

Referring to FIGS. 3A and 3B, water that is sourced from a water supply 302 (e.g., a municipal water system or a well) can be treated in a treatment system 210 to prepare it for use in an ethanol production process (for example, the ethanol production process 200A or 200B) or a steam generation system 304. The treatment system 210 can be used to reduce the level of contaminants (e.g., dissolved solids or suspended solids) that may be present in the water. The supply of water from the water supply 302 and treated water is balanced so that the soluble components in the water are maintained at a suitable level for the steam generation system 304, for the fermentation system 204 and for other plant systems.

Contaminants (e.g., dissolved solids) in water may cause hardness of water and may result in the forming of precipitate (e.g., scaling) on the surfaces of equipment and piping. The potential for scaling can be estimating by the Langelier Saturation Index, which is a calculation based on pH, total dissolved solids, alkalinity, temperature, and calcium-ion concentration. A high Langelier Saturation Index indicates a high probability of scaling. According to an embodiment, water from the water supply 302 that is fed into an ethanol production process (for example, the ethanol production process 200A or 200B) is balanced to minimize scaling and maximize water recycling. According to a preferred embodiment, the Langelier Saturation index of the water fed to the ethanol production process is less than 2.

Figure 4A:
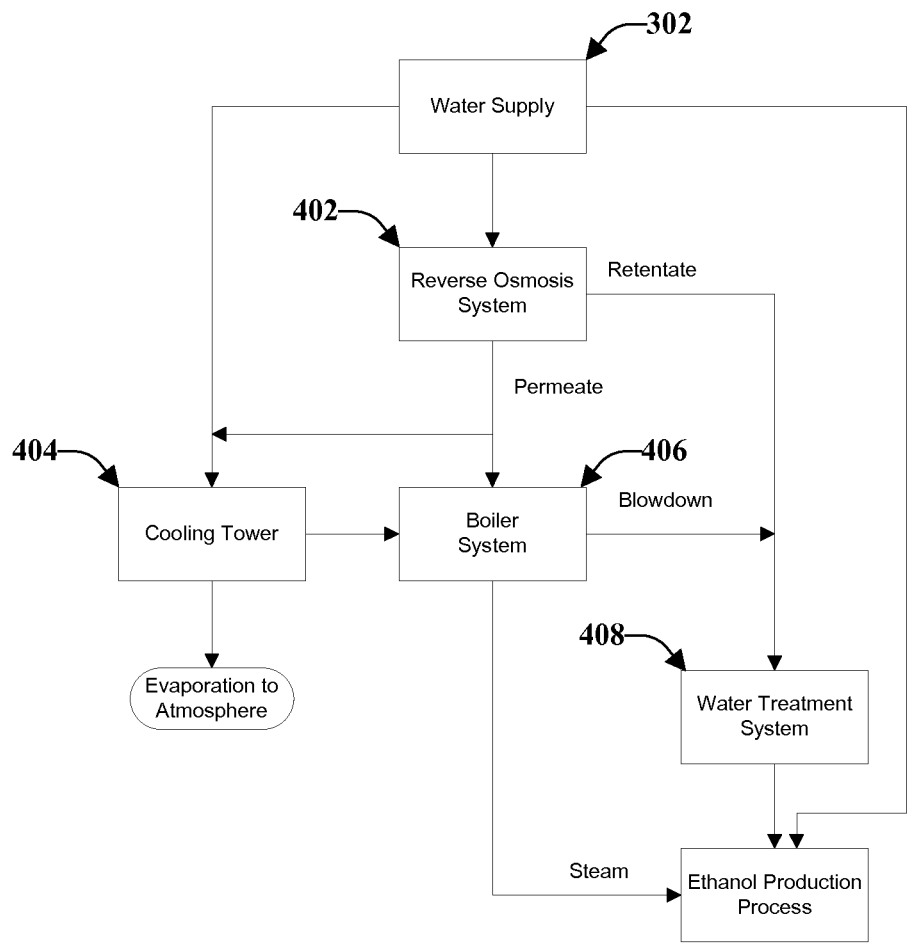
FIGS. 4A, 4B and 4C are schematic block diagrams of exemplary embodiments of water recycle systems for use in an ethanol production facility.
Figure 4B:
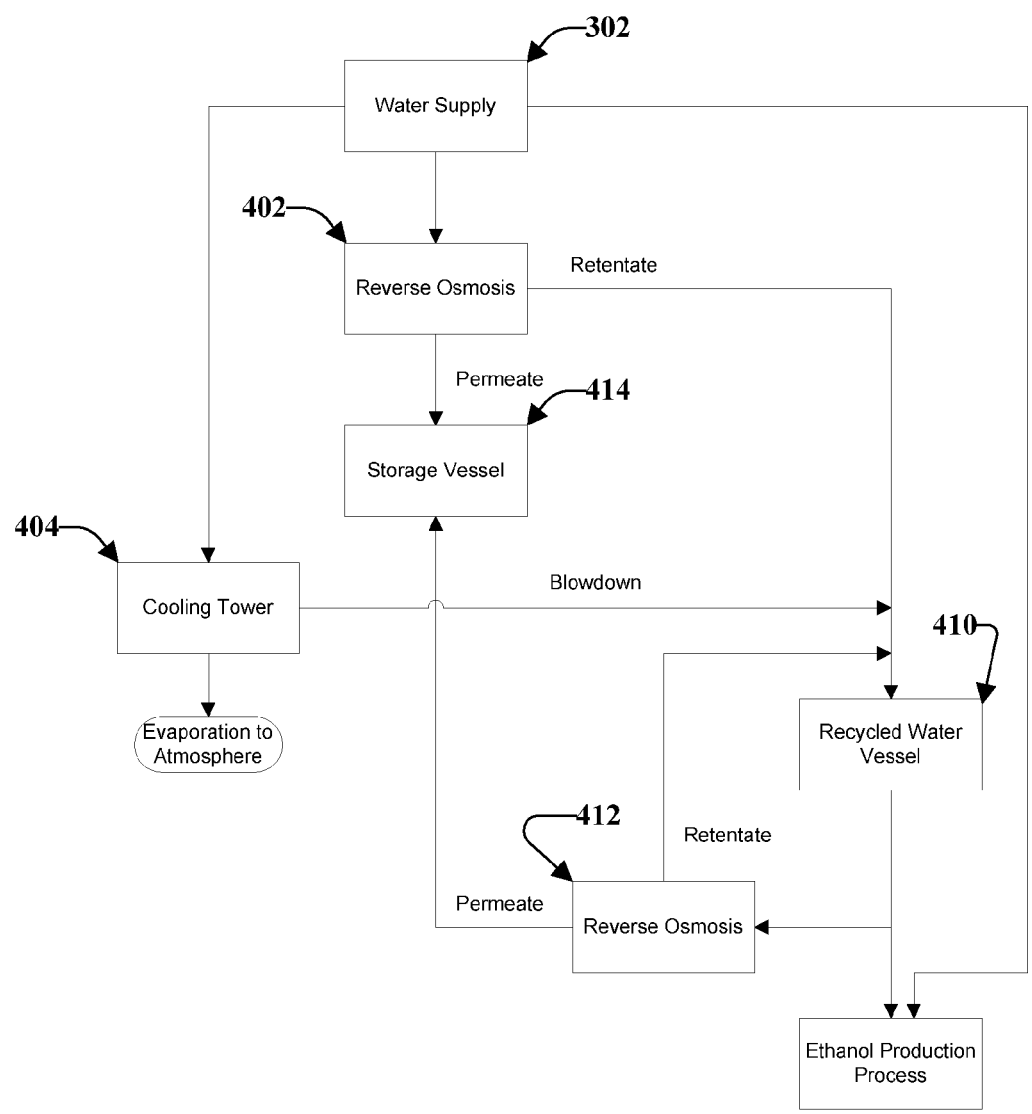
Figure 4C:
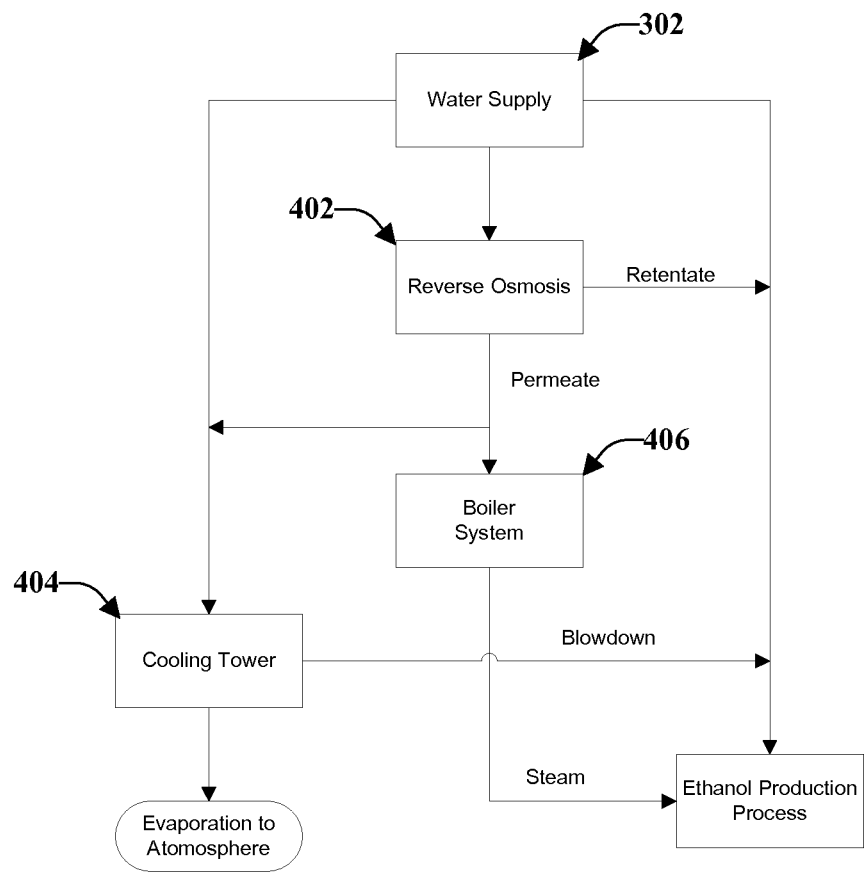

Referring to FIGS. 4A through 4C, exemplary embodiments of water recycle systems are shown. The water recycle system utilizes rejected waste water streams as a way to reduce overall water usage in the production of ethanol. The water recycle system may comprise a reverse osmosis system 402 and/or a cooling tower system 404. The steam generation system 304 may comprise a boiler system 406. The reverse osmosis system 402 may produce a permeate stream and a retentate stream. The permeate stream from the reverse osmosis system 402 may be used to feed the boiler system 406 and the cooling tower system 404.

As shown is FIG. 4A, according to an embodiment, water from the water supply 302 is supplied to the treatment system 210 (e.g., the cooling tower system 404 and/or the reverse osmosis system 402) and/or the ethanol production process (for example, as shown in FIGS. 2A and 2B). The reverse osmosis system 402 produces a retentate stream and a permeate stream. The retentate stream from the reverse osmosis system 402 may be sent to a second water treatment system 408, which may comprise a second reverse osmosis system. The treated retentate stream may be used to supplement the water supply to the fermentation system (e.g., as shown in FIGS. 2A and 2B). The permeate stream from the reverse osmosis system 402 can be used in the boiler system 406. The boiler system 406 may generate a water stream (e.g. blowdown) that can also be directed to the second water treatment system 408.

Referring to FIG. 4B, another embodiment of the water recycling system is shown. A retentate stream from the reverse osmosis system 402 and a water stream from the cooling tower system 404 (e.g. blowdown) are directed to a storage vessel 410 (e.g. recycled water vessel). Water from the recycled water vessel 410 may be directed to a second reverse osmosis system 412 or to the ethanol production process (e.g., as shown in FIGS. 2A and 2B). A retentate stream from the second reverse osmosis system 412 may be directed back in to the recycled water vessel 410, and a permeate stream from the second reverse osmosis 412 system may be directed to a storage vessel 414.

Referring to FIG. 4C, a preferred embodiment of the water recycling system is shown. Water from the water supply 302, a retentate stream from the reverse osmosis system 402, and discharge (e.g., blowdown) from the cooling tower system 404 are directed to the ethanol production process (e.g., as shown in FIGS. 2A and 2B). A permeate stream from the reverse osmosis system 402 is directed to the boiler system 406 and the cooling tower system 404. The relative amounts of water from each source are balanced so that a suitable composition of water is fed into the ethanol production process and that the water recycle can be maximized.

Referring to FIGS. 5-10, illustrated is an exemplary embodiment of a plant configured according to FIG. 4C. Water can be supplied to an ethanol production process (200A or 200B) from the water supply 302, the retentate stream from the reverse osmosis system 402, the permeate stream from the reverse osmosis system 402, and discharge from the cooling tower system 404 (e.g., blowdown). FIGS. 5-8 illustrate dissolved solids concentrations from source water from the water supply 302, from the retentate stream from the reverse osmosis system 402, from the permeate stream from the reverse osmosis system 402, and from discharge from the cooling tower system 404 (e.g., blowdown), respectively. FIG. 9 illustrates dissolved solids concentrations in water supplied to an ethanol production process (200A or 200B). FIG. 10 illustrates compositions of water supplied to the ethanol production process (200A or 200B) from the water supply 302, the retentate stream from the reverse osmosis system 402, the permeate stream from the reverse osmosis system 402, and discharge from the cooling tower system 404 (e.g., blowdown).

FIG. 5 illustrates dissolved solids concentrations in source water from the water supply 302 in an exemplary embodiment of a plant configured according to FIG. 4C. A typical operating range for the total dissolved solids concentration for the source water from the water supply 302 may be, for example, between 600 and 1500 parts per million. The total dissolved solids concentration may include between 90 and 200 parts per million Calcium (Ca), between 20 and 70 parts per million Magnesium (Mg), between 10 and 100 parts per million Sulfate ($SO_4$), between 20 and 70 parts per million Silicon Dioxide ($SiO_2$), and between 40 and 80 parts per million Chloride (Cl). In an exemplary embodiment, the total dissolved solids concentration for the source water from the water supply 302 may be 704 parts per million. In an exemplary embodiment, the total dissolved solids concentration may include 108 parts per million Calcium (Ca), 37 parts per million Magnesium (Mg), 24 parts per million Sulfate ($SO_4$), 32 parts per million Silicon Dioxide ($SiO_2$), and 45 parts per million Chloride (Cl).

FIG. 6 illustrates dissolved solids concentrations in the permeate stream from the reverse osmosis system 402 in an exemplary embodiment of a plant configured according to FIG. 4C. A typical range of the total dissolved solids concentration for the permeate stream from the reverse osmosis system 402 may be, for example, less than 20 parts per million. The total dissolved solids concentration may include less than 10 parts per million Calcium (Ca), less than 5 parts per million Magnesium (Mg), less than 2 parts per million Sulfate ($SO_4$), less than 4 parts per million Silicon Dioxide ($SiO_2$), and less than 10 parts per million Chloride (Cl). In an exemplary embodiment, the total dissolved solids concentration for the permeate stream from the reverse osmosis system 402 may be 18.5 parts per million. In an exemplary embodiment, the total dissolved solids concentration may include 2.5 parts per million Calcium (Ca), 0.9 parts per million Magnesium (Mg), 0.2 parts per million Sulfate ($SO_4$), 1.0 part per million Silicon Dioxide ($SiO_2$), and 1.9 parts per million Chloride (Cl).

FIG. 7 illustrates dissolved solids concentrations in the retentate stream from the reverse osmosis system 402 in an exemplary embodiment of a plant configured according to FIG. 4C. A typical operating range for the total dissolved solids concentration for the retentate stream from the reverse osmosis system 402 may be, for example, between 1500 and 3000 parts per million. The total dissolved solids concentration may include between 225 and 500 parts per million Calcium (Ca), between 50 and 175 parts per million Magnesium (Mg), between 60 and 125 parts per million Sulfate ($SO_4$), between 60 and 125 parts per million Silicon Dioxide ($SiO_2$), and between 100 and 250 parts per million Chloride (Cl). In an exemplary embodiment, the total dissolved solids concentration for the retentate stream from the reverse osmosis system 402 may be 2760 parts per million. In an exemplary embodiment, the total dissolved solids concentration may include 425 parts per million Calcium (Ca), 144 parts per million Magnesium (Mg), 293 parts per million Sulfate ($SO_4$), 124 parts per million Silicon Dioxide ($SiO_2$), and 174 parts per million Chloride (Cl).

FIG. 8 illustrates dissolved solids concentrations in discharge from the cooling tower system 404 in an exemplary embodiment of a plant configured according to FIG. 4C. A typical operating range for total dissolved solids concentration for the discharge (e.g. blowdown) from the cooling tower system 404 may be, for example, between 800 and 1500 parts per million. The total dissolved solids concentration may include between 100 and 200 parts per million Calcium (Ca), between 30 and 60 parts per million Magnesium (Mg), between 10 and 50 parts per million Sulfate ($SO_4$), between 10 and 60 parts per million Silicon Dioxide ($SiO_2$), and between 40 and 80 parts per million Chloride (Cl). In an exemplary embodiment, the total dissolved solids concentration for the blowdown from the cooling tower system 404 may be 876 parts per million. In an exemplary embodiment, the total dissolved solids concentration may include 130 parts per million Calcium (Ca), 48 parts per million Magnesium (Mg), 24 parts per million Sulfate ($SO_4$), 42 parts per million Silicon Dioxide ($SiO_2$), and 65 parts per million Chloride (Cl).

According to an exemplary embodiment, FIG. 9 illustrates ranges of dissolved solids concentrations of water fed to the ethanol production process (e.g., 200A or 200B) after recycling in an exemplary embodiment of a plant configured according to FIG. 4C. A typical operating range for total dissolved solids concentration in water fed to the ethanol process after recycling is between 1000 and 4000 parts per million. The total dissolved solids concentration may include between 100 and 600 parts per million Calcium (Ca), between 30 and 600 parts per million Magnesium (Mg), between 10 and 500 parts per million Sulfate ($SO_4$), between 0 and 125 parts per million Silicon Dioxide ($SiO_2$), and between 0 and 250 parts per million Chloride (Cl).

A preferred operating range for total dissolved solids concentration in water fed to the ethanol process after recycling, configured as in FIG. 4C, is between 1500 and 2500 parts per million. The total dissolved solids concentration may include between 250 and 450 parts per million Calcium (Ca), between 50 and 200 parts per million Magnesium (Mg), between 200 and 300 parts per million Sulfate ($SO_4$), between 60 and 110 parts per million Silicon Dioxide ($SiO_2$), and between 100 and 175 parts per million Chloride (Cl).

A most preferred operating range for total dissolved solids concentration in water fed to the ethanol process after recycling, configured as in FIG. 4C, is between 1800 and 2200 parts per million. The total dissolved solids concentration may include between 325 and 389 parts per million Calcium (Ca), between 100 and 150 parts per million Magnesium (Mg), between 225 and 275 parts per million Sulfate ($SO_4$), between 80 and 100 parts per million Silicon Dioxide ($SiO_2$), and between 125 and 160 parts per million Chloride (Cl).

According to an exemplary embodiment, configured as in FIG. 4C, the concentration of total dissolved solids is 2400 parts per million. The total dissolved solids concentration may include 368 parts per million Calcium (Ca), 125 parts per million Magnesium (Mg), 242 parts per million Sulfate ($SO_4$), 108 parts per million Silicon Dioxide ($SiO_2$), and 153 parts per million Chloride (Cl).

According to an exemplary embodiment configured as in FIG. 4C, as illustrated in FIG. 10, water may be supplied to the ethanol production process (e.g., 200A or 200B) from the water supply 302, the cooling tower system 404, the retentate stream from the reverse osmosis system 402 and steam as shown in FIG. 4C. According to an embodiment, water from the water supply 302 comprises up to 100 percent of the water supplied to the ethanol production process, discharge from the cooling tower system 404 comprises less than 10 percent of the water supplied to the ethanol production process, the retentate stream from the reverse osmosis system 402 comprises less than 30 percent of the water supplied to the ethanol production process, and steam comprises between 0 and 5 percent of the water supplied to the ethanol production process.

In a preferred embodiment configured as in FIG. 4C, the water from the water supply 302 comprises between 60 and 90 percent of the water supplied to the ethanol production process. discharge from the cooling tower system 404 comprises between 1 and 7 percent of the water supplied to the ethanol production process, the retentate stream from the reverse osmosis system 402 comprises between 10 and 25 percent of the water supplied to the ethanol production process, and steam comprises between 1 and 3 percent of the water supplied to the ethanol production process.

In a most preferred embodiment configured as in FIG. 4C, water from the water supply 302 comprises between 70 and 80 percent of the water supplied to the ethanol production process, discharge from the cooling tower system 404 comprises between 2 and 4 percent of the water supplied to the ethanol production process, the retentate stream from the reverse osmosis system 402 comprises between 15 and 20 percent of the water supplied to the ethanol production process, and steam comprises between 1.8 and 2.2 percent of the water supplied to the ethanol production process.

The embodiments as disclosed and described in the application (including the FIGS. and Examples) are intended to be illustrative and explanatory of the present inventions. Modifications and variations of the disclosed embodiments, for example, of the apparatus and processes employed (or to be employed) as well as of the compositions and treatments used (or to be used), are possible; all such modifications and variations are intended to be within the scope of the present inventions.

I claim:

1. A method of recycling water in a biorefinery ethanol production process, the method comprising:
   supplying water from a water supply to a reverse osmosis system of the biorefinery ethanol production process;
   supplying water from the water supply and the reverse osmosis system to a cooling tower of the biorefinery ethanol production process;
   supplying water from the reverse osmosis system to a boiler system of the biorefinery ethanol production process; and
   supplying steam from the boiler system and water from the cooling tower and the reverse osmosis system to the biorefinery ethanol production process.

2. The method of claim 1, wherein the water from the water supply comprises less than 100 percent of water supplied to the biorefinery ethanol production process.

3. The method of claim 1, wherein the water from the cooling tower comprises between 1 and 7 percent of water supplied to the biorefinery ethanol production process.

4. The method of claim 1, wherein water supplied to the biorefinery ethanol production process, after recycling said water, comprises between 100 and 600 parts per million of Calcium.

5. The method of claim 1, wherein water supplied to the biorefinery ethanol production process, after recycling said water, comprises between 30 and 600 parts per million of Magnesium.

6. The method of claim 1, wherein water supplied to the biorefinery ethanol production process, after recycling said water, comprises between 10 and 500 parts per million of Sulfate.

7. The method of claim 1, wherein water supplied to the biorefinery ethanol production process, after recycling said water, comprises between 0 and 125 parts per million of Silicon Dioxide.

8. The method of claim 1, wherein water supplied to the biorefinery ethanol production process, after recycling said water, comprises between 0 and 250 parts per million of Chloride.

9. The method of claim 1, wherein water supplied to the biorefinery ethanol production process, after recycling said water, comprises between 1000 and 4000 parts per million of total dissolved solids.

10. The method of claim 1, wherein the reverse osmosis system produces a permeate stream and a retentate stream, the retentate stream being supplied to the biorefinery ethanol production process.

11. The method of claim 1, wherein the water supplied to the biorefinery ethanol production process comprises a Langelier Saturation Index less than 2.

* * * * *